US010823724B2

(12) United States Patent
Love (10) Patent No.: US 10,823,724 B2
(45) Date of Patent: Nov. 3, 2020

(54) SYSTEM AND METHOD FOR TRAILING A WOUNDED ANIMAL

(71) Applicant: Jeff Love, Georgetown, TX (US)

(72) Inventor: Jeff Love, Georgetown, TX (US)

( * ) Notice: Subject to any disclaimer, the term of this patent is extended or adjusted under 35 U.S.C. 154(b) by 268 days.

(21) Appl. No.: 15/925,092

(22) Filed: Mar. 19, 2018

(65) Prior Publication Data
US 2018/0267017 A1    Sep. 20, 2018

Related U.S. Application Data

(60) Provisional application No. 62/473,743, filed on Mar. 20, 2017.

(51) Int. Cl.
*G01N 33/50* (2006.01)
*G01N 33/00* (2006.01)
*G01J 3/10* (2006.01)
*G01N 21/29* (2006.01)
*G01J 3/02* (2006.01)
*G01N 21/25* (2006.01)

(52) U.S. Cl.
CPC ............ *G01N 33/50* (2013.01); *G01J 3/0272* (2013.01); *G01J 3/10* (2013.01); *G01N 21/25* (2013.01); *G01N 21/29* (2013.01); *G01N 33/0047* (2013.01); *G01N 33/0054* (2013.01); *G01N 2201/0221* (2013.01); *Y02A 50/246* (2018.01)

(58) Field of Classification Search
CPC  C12Q 1/54; C12Q 1/26; B01L 3/5029; B01L 2300/021; B01L 2300/025; C12Y 101/03004; G01N 2021/7759; G01N 2035/00108; G01N 2021/7776; G01N 2001/002; G01N 35/00871; G01N 21/78; G01N 1/00; G06T 2207/10024; G06T 7/90; G06T 2207/30024
See application file for complete search history.

(56) References Cited

U.S. PATENT DOCUMENTS

| | | | | |
|---|---|---|---|---|
| 5,859,362 | A * | 1/1999 | Neudorfl | G01N 1/2214 73/23.2 |
| 8,399,262 | B2 * | 3/2013 | Mazzari | G01N 27/126 436/525 |
| 9,696,261 | B2 * | 7/2017 | Tokhtuev | G01N 21/78 |
| 2006/0044792 | A1 * | 3/2006 | Dallas | G01N 21/29 362/184 |
| 2006/0266102 | A1 * | 11/2006 | Tolliver | G01J 3/02 73/23.2 |

(Continued)

OTHER PUBLICATIONS

Detecting365 (Proper Metal Detecting Swing, Getting Started Detecting, http://detecting365.com/metal-detector-proper-swing-2/, 2013 (Year: 2013).*

(Continued)

*Primary Examiner* — Benjamin R Whatley
*Assistant Examiner* — Jean Caraballo-Leon
(74) *Attorney, Agent, or Firm* — Becker Patent Law, LLC (57) ABSTRACT

A system and method of trailing a wounded animal includes sensing a chemical component of mammalian blood and other bodily fluids in the air using a sensing device. The sensing device comprises a housing configured to be held in a hand of a person trailing the wounded animal. An audible and/or visual indication is provided based on the sensed chemical component.

20 Claims, 3 Drawing Sheets

(56) References Cited

U.S. PATENT DOCUMENTS

| | | | | |
|---|---|---|---|---|
| 2007/0056388 | A1* | 3/2007 | Henry | G01N 1/24 |
| | | | | 73/863.12 |
| 2012/0272713 | A1* | 11/2012 | Kountotsis | G01N 33/497 |
| | | | | 73/23.3 |
| 2015/0308999 | A1* | 10/2015 | Villareal Guerra | ............ |
| | | | | G01N 33/0001 |
| | | | | 73/23.34 |
| 2016/0018371 | A1* | 1/2016 | Acharya | G01N 33/497 |
| | | | | 436/110 |

OTHER PUBLICATIONS

RAE Systems—Mini RAE Lite User Guide—2011 (Year: 2011).*
ScenTrak—Tufts Journal Web Page—2008 (Year: 2008).*
CogniScent Press Release—BusinessWire—2006 (Year: 2006).*
Product Information Sheet, TGS 2602 by Figaro USA Inc, 2 pages (previously submitted by Applicant, cited again to include the publication year into the record). (Year: 2005).*
Poster, "Characterization of specific volatiles of pig blood with the potential as predator chemoattractants and as prey warning signals," Shiva Krishna Rachamadugu, IFM, Biology-Master Thesis (2012), 1 page.
"Sniffer technology' may replace detection dogs," Homeland Security News Wire, printed from the Internet Mar. 20, 2017, 2 pages.
"Chemical sensor on a chip created to test chemical composition of liquids," ScienceDaily, Jun. 11, 2014, Vienna University of Technology, 5 pages.
"Pets' Amazing Abilities," Daphne Sashin, WebMD Pet Health Feature, printed Mar. 17, 2017 from http://pets.webmd.com/features/petsamazingabilities, 4 pages.
SainSmart MQ138 Formaldehyde Aldehydes Gas Detection Sensor Module, printed from https://www.sainsmart.com/sensors/eco/sainsmartmq138formaldehydealdehydesgasdetectionsensormodule.html on Mar. 17, 2017, 2 pages.
Nilsson S, Sjöberg J, Amundin M, Hartmann C, Buettner A, Laska M (2014) Behavioral Responses to Mammalian Blood Odor and a Blood Odor Component in Four Species of Large Carnivores. PLoS ONE 9(11): e112694. doi:10.1371/journal.pone.0112694, 10 pages.
"Field Asymmetric Ion Mobility Spectrometry (FAIMS)," Owlstone.
Investigación y Desarrollo. "Electronic nose could aid in rescue missions." ScienceDaily. ScienceDaily, Jul. 23, 2014. <www.sciencedaily.com/releases/2014/07/140723110403.htm>, 4 pages.

* cited by examiner

SYSTEM AND METHOD FOR TRAILING A WOUNDED ANIMAL

CROSS REFERENCE TO RELATED APPLICATIONS

This application claims the benefit of U.S. Provisional Application No. 62/473,743, filed Mar. 20, 2017, which is incorporated by reference herein in its entirety.

BACKGROUND

The wounding and loss of animals has been problematic from human's earliest hunter-gatherer beginnings. Hunting has evolved from being purely for survival to modern day sport and recreation. While food is still important, other factors such as trophy hunting also play an important modern role. The risk of losing a wounded animal remains as a significant negative for hunting today. Ending any suffering of the animal, loss of a trophy, and loss of the food source are all strong motivators for being able to retrieve a wounded animal.

Trailing (including tracking or otherwise following a wounded animal) wounded animals is a learned skill. Often there is no continuously visible blood trail. A hunter learns to look for spots and flecks of blood as confirmation that the hunter is still on the proper track. Sometimes, there are significant distances between locations of visible blood. At trail junctures, one frequently has to search each branch until blood can confirm which path the animal has taken. When a blood trail is "lost" the common procedure is to return to the last spot of blood and begin a much more circumspect search. Even the smallest fleck of fresh blood serves as confirmation that the animal passed that direction.

Unless blood has fallen onto highlighting background, such as a white rock or green leaf, even a large spot can be hard to detect as it often blends in with the background, especially after a period of oxidation.

DETAILED DESCRIPTION OF ILLUSTRATIVE EMBODIMENTS

One or more embodiments described herein may detect certain chemicals in mammalian blood and/or other bodily fluids.

One or more embodiments described herein may use volatile organic compounds to follow blood and/or bodily-fluid trails of animals.

One or more embodiments described herein may provide an improved method for trailing wounded animals with the use of scent, aroma, an electronic nose, or other airborne compound detectors.

One or more embodiments may improve the process of trailing animals in areas with difficult terrain and/or fauna using chemical detection.

One or more embodiments may use a chemical sensing device configured to be sensitive to small amounts of blood.

One or more embodiments may use a sensor to simulate olfaction of dogs, humans or other mammals.

One or more embodiments described herein may assist the visual component of tracking wounded animals through highlighting tiny amounts of bodily fluids.

One or more embodiments described herein may detect chemicals in mammalian blood and/or other bodily fluids that have been altered in chemical composition due to exposure to the atmosphere, such as from oxidation.

One or more embodiments described herein may provide an improved method of trailing wounded animals with the use of a laser light detector.

One or more embodiments may use scent identification of individual animals through recognition of unique chemical signatures of the animal.

Figure 1:
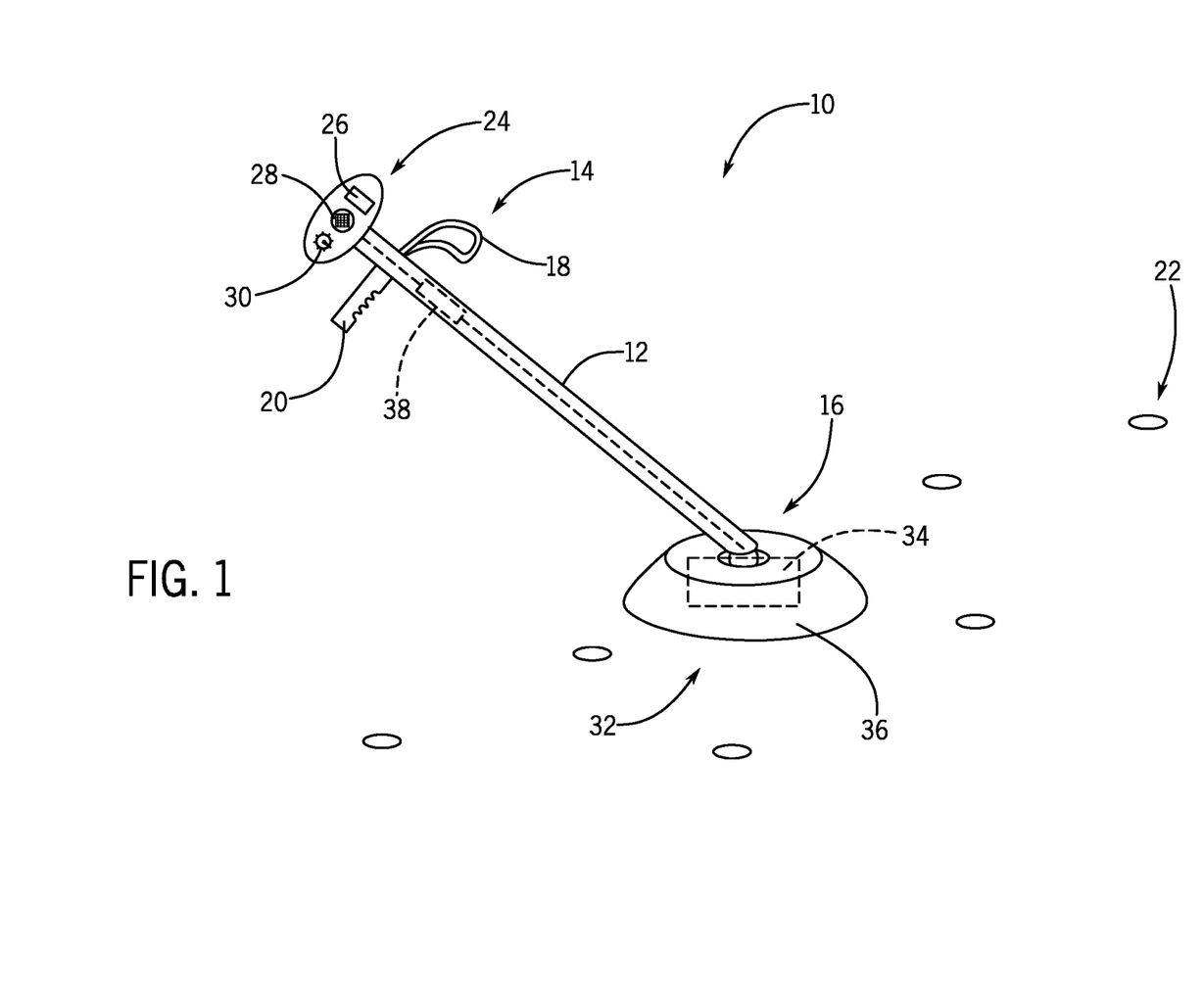
FIG. 1 is a schematic diagram of an apparatus for assisting a person in trailing a wounded animal, according to an illustrative embodiment.

Referring now to FIG. 1, an apparatus and method for assisting a person in trailing a wounded animal will be described. The apparatus may be configured to be operable by a human person, such as a hunter, while in an outdoors environment, such as a field, forest, or other area where animals are hunted, trailed, tracked, etc. The apparatus may be hand-held and may, for example, weigh less than about 20 pounds, less than about 10 pounds, or even less than about 5 pounds. The apparatus or sensing device 10 may comprise an elongated housing 12, which may be tubular or solid, comprising a first portion 14 configured to be held in a person's hand and a second portion 16 opposite the first portion. The housing may be at least about 1-2 feet long and may also be narrow in width, such as less than about 10 inches wide, or less than about 4 inches wide. In one advantageous embodiment, the housing is at least three feet long so that a user in a standing position may comfortably hold the housing on one end while sweeping the opposite end of the housing over the ground. The housing may have one or more features making it portable, such as a telescoping body, foldable components, detachable portions, etc., to facilitate ease of transport.

First portion 14 of housing 12 is disposed on, near, or in the vicinity of a first end of the housing designed to interface with the human operator. First portion may comprise one or more mechanical handles such as a loop handle 18, a grip 20 (such as a pistol grip), or other handles. The handles may be sized and shaped to allow a human operator to firmly grip apparatus 10 and to manipulate apparatus 10 in sweeping motions in search of a trail of bodily fluids 22. First portion 14 may further comprise a user interface portion 24, which may comprise one or more of a display 26, a speaker 28, and a mechanically-operable user input device 30, such as a button, dial, rotary switch, touch screen, etc.

Second portion 16 may comprise an air inlet 32, which may be wide or narrow. Air inlet 32 may be any aperture, orifice, or other opening in housing 12 or a component coupled to housing 12 in contact with ambient air. A sensor 34 may be disposed near the air inlet in a configuration to be in contact with the ambient air, to enable the sensor to sense chemical components in the ambient air. A shroud or concentrator 36 may be disposed around sensor 34 to assist in concentrating the chemical components and/or directing the chemical components toward sensor 34. Shroud 36 may comprise a flexible material, such as a rubber or other polymer skirt, configured to be define a headspace which is dragged along or near the ground during the advantageous methods described herein. In some embodiments, a fan may be disposed at second end 16 to pull in ambient air and direct the ambient air toward or draw the air across sensor 34.

Sensor 34 may in some cases be disposed further up housing 12 within a channel or hollow portion within second end 16 of housing 12. The powered fan may be configured to direct air toward or across sensor 34 and then out an exhaust outlet in second portion 16 to improve performance of the sensor.

A control circuit 38 may be disposed within housing 12. Control circuit 38 may comprise discrete analog and/or digital components configured to perform the functions described herein. Control circuit 38 may be coupled to sensor 34 and may be configured to provide an audible and/or visual indication via user interface 24 based on a sensed chemical component, temperature, humidity, or other sensed characteristics of air in the vicinity of sensor 34. For example, if the quantity of sensed chemical exceeds a predetermined threshold, control circuit 38 may be configured to provide the indication as an alert, alarm or other indication that the bodily fluid has been detected. In some embodiments, both an audible and visual indication are provided, to assist the operator.

A battery (not shown) is coupled to control circuit 38 (and optionally to the fan, sensor 34, user interface 24, etc.) and is configured to provide power to control circuit 38. The battery may be rechargeable by way of a suitable wall charging device. The battery may use Lead Acid, Nickel Cadmium, Nickel-Metal Hydride, Lithium Ion, Lithium Ion Polymer, and/or other energy storage technologies. The battery may be disposed within the housing, e.g., recessed within the housing, completely encased in the housing, disposed apart from the housing and connected by a wire or power cable, etc.

While a hand-held device may be used along with an operation of sweeping back and forth close to the ground, other mechanical structures are contemplated.

In some embodiments, a manually-operable input device 30 is coupled to the control circuit. The control circuit is configured to adjust a sensitivity of sensing device 34 or the aforementioned predetermined threshold based on a signal from the manually-operable input device. Sensitivity may be adjusted in any of a number of manners. For example, sensitivity may be adjusted by setting the predetermined threshold of chemical present beyond which an indication will be provided. Alternatively, sensitivity may be adjusted by increasing a gain on an amplifier circuit configured to receive the sensed signal and transmit the sensed signal to control circuit 38. In some embodiments, a squelch circuit may be used to suppress the indication in the absence of a sufficiently strong desired input signal. Other circuits and techniques for sensitivity adjustment may be employed in various embodiments.

A sensitivity control circuit may be configured to eliminate unwanted signal. The sensitivity control circuit may be configured to abate a signal produced in the presence of or in response to an unwanted naturally occurring chemical compound, such as a compound associated with grass, dirt, flowers, etc.

In some embodiments, the sensor and/or control circuit may be configured to detect one or more chemical components unique to or characteristic of the presence of one or more taxonomic ranks, such as species, genus, family, order, class, phylum and/or kingdom, or an organ, tissue, bodily fluid, or other portion thereof.

Sensor 34 and/or control circuit 38 may be configured to detect a presence of a trail of bodily fluids 22 having one or more different chemical components or other characteristics, and sensing technologies. Sensor 34 may act as an electronic nose, using sensors that mimic the nostrils of a human, dog, or other mammal. Sensor 34 may detect an odorant, an aroma, a scent, an airborne chemical compound, a volatile organic compound, an aroma-compound, a fragrance, a flavor, a humidity, a temperature, etc. A chemical compound has a smell or odor when it is sufficiently volatile to be transported to the olfactory system in the upper part of the human nose. An electronic nose may be a device intended to detect odors or flavors.

In one example, the presence of trans-4,5-epoxy-(E)-2-decenal may be detected. See, for example, Nilsson et al, "Behavioral Responses to Mammalian Blood Odor and a Blood Odor Component in Four Species of Large Carnivores," published Nov. 10, 2014 at http://dx.doi.org/10.1371/journal.pone.0112694. trans-4,5-Epoxy-(E)-2-decenal is an oxygenated $\alpha,\beta$-unsaturated aldehyde found in mammalian blood that gives blood its characteristic metallic odor. It is used by predators to locate blood or prey. In another example, the presence of any aldehydes may be detected.

In another example, the presence of Oct-1-en-3-one may be detected. Oct-1-en-3-one ($CH_2$=$CHC$(=$O$)($CH_2$)$4CH_3$), also known as 1-octen-3-one, is an odorant that is responsible for the typical "metallic" smell of metals and blood coming into contact with skin. Oct-1-en-3-one has a strong metallic mushroom-like odor with an odor detection threshold of 0.03-1.12 µg/m3. In another example, the presence of any ketones may be detected.

In other examples, any compounds including androstenone, androstadienone and/or other steroidal pheromones may be detected and be indicative of a wounded animal.

In other examples, 2,3 butadione (butter like) (Z)-1,5-octadien-3-one (green like), 3-methylthio propanal (cooked potato like), nonanoic acid (fatty or plastic like), acetic acid (vinegar like) and p-cresol (horse stable-like) are more examples of olfactory sensitive compounds in blood.

In other examples, sensors can be configured to sense the presence of saturated and/or unsaturated aldehydes and ketones, alcohols and their isomers, alkanes, carboxylic acids, terpenes, sulphur-containing compounds, aromatic compounds, and other compounds.

In other examples, sensors may be configured to detect volatile fatty acids, such as acetate, propionate, butyrate, lactate, etc.

Sensors may be configured to detect volatile organic compounds, such as carbon dioxide, methane, ammonia, etc.

Other chemical compounds in bodily fluids of mammals or other hunted game may be now known or later discovered to be sufficiently volatile so as to be detected by current sensing technologies or future sensing technologies. For example, the presence of chyme may be detected by a sensor. Chyme is a pulpy acidic fluid that passes from the stomach to the small intestine, consisting of gastric juices and partly digested food. Other partially digested chemical components may be detected.

In some embodiments, the sensor(s) and corresponding processing circuit may be configured to quantify smells produced by bacteria or a microbiome.

Some animals with stomach and/or visceral wounds have a very distinct and strong odor which may make those bodily fluids good candidates for detection.

In some embodiments, feces odor components may be detected, such as methanethiol, dimethyl sulfide, dimethyl trisulfide, dimethyl disulfide, indole, skatole, hydrogen sulfide, etc.

Some chemical compounds that may be detected by the embodiments described herein may be a component, result or bi-product of exposure of a bodily fluid or other portion of a wounded animal to the atmosphere, such as by way of oxidation. Scents of chemical compounds created as a result of oxidation and/or decomposition of bodily fluids may be more concentrated, more pungent, or otherwise more detectable in some circumstances than scents created by the bodily fluids themselves.

Sensor 34 and/or circuit 38 may employ any of a number of different sensing technologies. Sensor 34 may be configured to detect one or more volatile organic compounds (VOCs). VOCs in the environment can be detected based on different principles and interactions between the organic compounds and the sensor components. Some electronic devices may detect part per million (ppm) concentrations despite having low selectivity. Other electronic devices can predict with reasonable accuracy the molecular structure of the VOCs and/or may be used to identify a fingerprint or signature of a scent, odor or chemical in the ambient air.

In one embodiment, a broad-spectrum detector may be utilized with adjustable sensitivity to abate unwanted signal. Advantageously, a broad-spectrum detector may be a low cost option and may be available commercially off-the-shelf. In one embodiment, a SainSmart MQ138 Formaldehyde Aldehydes Gas Detection Sensor Module may be used, manufactured by Shenzhen Prophet Technology Co., Limited, Guangdong, China. The sensor may be a discrete, analog, and/or surface mount component disposed on a printed circuit board.

In another embodiment, a selective sensor may be used, which may be designed or programmed in such a manner where only one (or a few) critical compounds will be detected. In this case, highly specific detection can be tailored to maximize desired signal and eliminate or abate the collection of unwanted signal.

In another embodiment, a sensor configured for direct injection mass spectrometry (DIMS) may be used. Direct injection mass spectrometry techniques may provide for rapid detection and accurate quantification of VOCs. DIMS may include mass-spectrometry-e-noses, atmospheric-pressure chemical ionization (APCI), proton-transfer-reaction mass spectrometry (PTR-MS), selected ion-flow-tube mass spectrometry (SIFT-MS), and other techniques. PTR-MS instruments based on time-of-flight mass spectrometry may reach detection limits of 20 pptv (parts per trillion by volume) after 100 ms and 750 ppqv (parts per quadrillion by volume) after 1 minute measurement (signal integration) time. The mass resolution of these devices may be between 7000 and 10,500 m/$\Delta$m, thereby making it possible to separate some isobaric VOCs and quantify them independently.

A sensor configured for field asymmetric ion mobility spectrometry (FAIMS) may be used, such as the Owlstone FAIMS chip, manufactured by Owlstone Inc., Norwalk, Conn. A FAIMS sensor may be configured to detect multiple gases simultaneously in under a second at detection levels below part per billion (ppb). The sensor may be programmable to detect new gases through software.

In another embodiment, a metal-oxide-semiconductor (MOS) sensor, such as a FIGARO TGS 2602 air contaminant sensor may be used, which is manufactured by FIGARO USA, Inc., Arlington Heights, Ill. The TGS 2602 has high sensitivity to low concentrations of odorous gases such as ammonia and $H_2S$. The sensor also has high sensitivity to low concentrations of VOCs such as toluene. The TGS 2602 may be used with a microprocessor (FIC02667) which contains special software for handling the sensor's signal. The sensor may be used with a heater device and may be housed in a standard TO-5 package.

In other embodiments, other MOS sensors may be used to sense characteristics of a trailed animal.

In one embodiment, control circuit 38 may be configured to filter a signal from the sensing device. The device may comprise a memory configured to store a signature representing sensed data for the blood or other bodily fluid to be trailed. The control circuit may be configured to receive sensed data, compare the sensed data to the signature, and provide the indication based on a result of the comparison.

In some embodiments, control circuit 38 may be programmed with an algorithm that allows the discrimination of odors.

A sensor configured to use laser light to detect or sense chemicals emitted by mammalian blood and/or other bodily fluids may be used in some embodiments. In one example, a quantum cascade laser (QCL) device may be used, such as one made by Cascade Technologies Ltd., Stirling, Scotland. In one example, a laser and a corresponding light detector may be disposed on a single chip. The light is transported from the laser to the detector on a specially designed waveguide, which may have a gap therebetween of about 50 micrometers or less. The chip can measure the chemical composition of a liquid in which the chip is submerged. A similar principle or device may be directed to detecting chemical composition of air. In some cases, the sensor may be configured to use spectroscopy to absorb samples in sub-parts per billion.

In another example, a camera may be used to detect a color of the ground being swept by the apparatus. The camera may be coupled with a light source for illuminating the ground. The camera may detect colors and use image processing algorithms to identify a color indicative of a blood trail (e.g., red). The camera may and associated processing circuit may determine spectral or colorimetric values of the ground, converting each spectral or colorimetric value obtained into a CIE XYZ value, converting each CIE XYZ value into CIE L*a*b* values, or using other color spaces values. Data from the camera and determinations from the circuit may be used along with data from the other sensors described herein to determine the presence or absence of an animal being trailed.

Sensor 34 may comprise one, at least two, at least three, or more of the different sensors and/or sensing technologies described herein. For example, sensor 34 may comprise a first sensor configured to detect the presence of VOCs, a second sensor configured to detect humidity, and a third sensor configured to detect the presence of ammonia. One or more sensed signals may be used to improve the sensing of other components, for example where humidity sensor data may be used to calibrate or improve the data generated from sensing VOCs or another compound. In one example, an alarm or alert is triggered when data from a first sensor reaches a first threshold AND data from a second, different type of sensor reaches second, different threshold; wherein if only one of these sensor reaches its corresponding threshold, the alarm or alert is not triggered.

Figure 3:
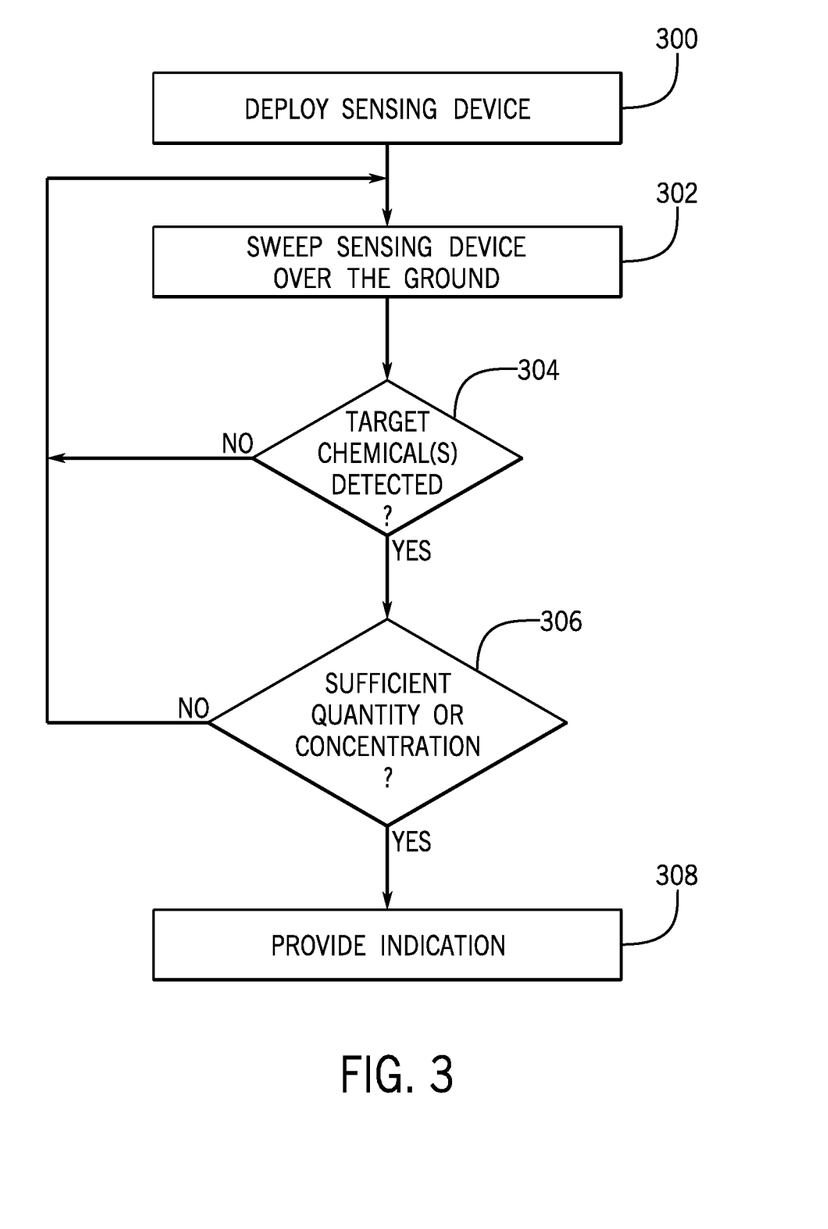
FIG. 3 is a flowchart of a method of trailing a wounded animal, according to an illustrative embodiment.

Referring now to FIG. 3, a method of trailing a wounded animal will be described, according to an exemplary embodiment. At a block 300, a hunter or other person deploys a sensing device. The sensing device may be retrieved from a bag or pack, and may comprise a shoulder strap for ease of carrying. The deployment may comprise one or more of telescoping an elongated housing, assembling different components or portions of the sensing device, activating an on/off switch, adjusting a sensitivity, or other deployment steps.

At a step 302, the sensing device is swept over the ground in an area where a wounded animal is believed to have traversed. The sensing device may be swept back and forth over different areas of the ground. During this step, the sensor or sensors on the sending device are active, powered and sensing for the presence of an airborne chemical compound, such as a volatile organic compound, and/or other characteristics of the trailed animal and ambient air nearby. The sensing device is disposed within about 10 inches of the ground, within about 8 inches of the ground, or within about 4 inches of the ground in various embodiments.

At a block 304, the sensing device is configured to determine whether a chemical or chemicals of interest (i.e., a target chemical) is detected. If not, the person continues sweeping over the ground.

If the target chemical is detected, processing proceeds to block 306 in which the sensing device and/or processing circuit determines whether a sufficient quantity or concentration has been detected. This determination may be made using discrete circuit components disposed on a printed circuit board or using a programmed processor configured to receive data indicating the quantity or concentration of the component sensed and to compare the quantity to a predetermined value stored in memory. If an insufficient quantity or concentration is detected, the person continues sweeping over the ground.

If a sufficient quantity or concentration is detected, the sensing device is configured to provide the audible and/or visual indication to the person. This indicates to the person that the trail has been found. The person may then continue sweeping in the direction that the trail leads to find the next part of the trail.

In some embodiments, sensing device 10 may further comprise a second detecting system based on reflected light to further aid in the detection of bodily fluid trail 22. The second detecting system may share circuit components with the system shown in FIGS. 1 and 2 herein, such as a control circuit, battery, input device, etc. The second detecting system may comprise one or more light transmitters and light receivers configured to illuminate the ground or brush near the second end 16. Upon reflection of light indicative of the presence of a bodily fluid (e.g., with certain reflectivity and/or color, etc.) the control circuit of the sensing device 10 may provide an indication of the presence of the bodily fluid. The sensing device may provide the indication if either a chemical compound aroma is sensed or if the light sensor indicates the presence of mammalian bodily fluid. Alternatively, the sensing device may be programmed to provide the indication only in the presence of both aroma and light sensor data indicating the presence of mammalian bodily fluid. Alternatively, various weighted schemes may be applied to the two or more sensor inputs to make a determination as to whether a bodily fluid is sensed with a predetermined degree of certainty.

In some embodiments, more than two sensing techniques described herein may be used. For example, a discrete formaldehyde sensor, a sensor for detecting reflected light, and a laser light sensor for detecting chemical components in the air may all be used in a single housing or detection tool. Each sensor may have a distinct notification or alarm provided to the user (e.g., audible and/or visual), and/or the control circuit may be configured to generate a composite score based on data from the three or more sensors and provide a notification when the composite score exceeds a predetermined composite score.

While the exemplary embodiments have been described with reference to the tracking of a hunted animal and game retrieval, the teachings herein may be applied to other methods, systems and fields, such as in law enforcement and military applications (dealing with human mammals). The target airborne chemical may be a chemical found in human blood to assist in trailing a wounded soldier, a perpetrator of a crime, etc.

Figure 2:
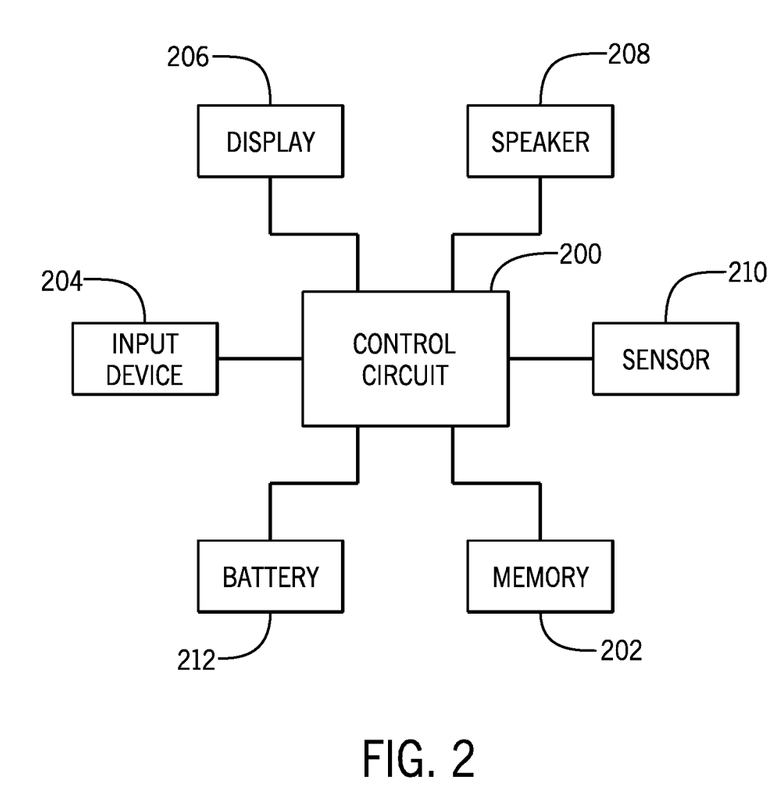
FIG. 2 is a block diagram of an apparatus and method assisting a person in trailing a wounded animal, according to an illustrative embodiment.

FIG. 2 is a block diagram of an electronic circuit, processing circuit, or control circuit for processing sensed data, according to an illustrative embodiment. The blocks in FIG. 2 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, surface-mount components, and/or other circuit components.

As shown in FIG. 2, the system may comprise a control circuit 200, which can be any suitable processor, processing unit, or microprocessor, for example. A memory 202 may comprise any type of volatile and/or non-volatile memory such as, for example, static random access memory (SRAM), dynamic random access memory (DRAM), flash memory, read-only memory (ROM), hard disk drives, optical drives, tape storage devices, etc. Memory 202 may comprise a tangible medium for storing executable instructions to be executed by control circuit 200.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

One or more of the system, apparatus, and/or article of manufacture components described above, or parts thereof, can be implemented using instructions, code, and/or other software and/or firmware, etc. stored on a tangible machine accessible or readable medium and executable by, for example, a processor system. Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

Control circuit 200 may be configured to communicate with an input device 204, which may comprise one or more dials, switches, buttons, keyboards, a touch screen display, etc. Control circuit 200 may be configured to send display signals and/or data to display 206. Display 206 may comprise one or more light-emitting diodes, a liquid crystal display, or other display technologies. Displayed data may include an indication that a sensed chemical component has been detected at all, an indication that the chemical has been detected in excess of a threshold, a quantity of chemical detected (e.g., in parts per billion or other units), or an instruction ("TRAIL FOUND"). A speaker 208 may comprise any type of device configured to provide an audible signal, such as a buzzer, speaker, vibrator, or other device. Sensor 210 and battery 212 have been described previously herein.

EXAMPLE

A test was conducted to demonstrate that a portable sensing device could be used to detect volatile organic compounds (VOC) from mammalian body fluids or other components.

A large, semi-eviscerated opossum, with entrails visible, was placed in a plastic bag for transport and testing. The test instrument comprised a UNI-T UT-338C Series portable air quality detector, sold by Uni-Trend Technology (China) Ltd., China, which conducts real-time comparison of air quality of current environment. The instrument has a large-screen liquid crystal display with backlight and is powered by a rechargeable lithium battery. The instrument is small and compact, measuring approximately 5 inches×3 inches× 1.5 inches. The instrument is configured to measure multiple parameters including temperature, humidity and particulate concentration (PM 2.5). The instrument also meters volatile organic compounds (VOC) with sensitivity mg/m$^3$ (within a metering range of 0.1 to 9.9).

The instrument was placed in a clean plastic bag identical to the one containing the opossum as a control measure to show there were no VOCs released by the plastic. The bag containing the opossum was then opened and the instrument was lowered inside. The instrument indicated a strong response. From a distance of more than 1 foot above the opossum, the displayed VOC reading pegged at 9.9 as the bag concentrated the VOCs. The opossum was then removed from the bag and placed on the ground. The meter was lowered from a starting height of approximately 2 feet. At a distance of about 8 to 10 inches from instrument to opossum, the displayed VOC reading was weak and sporadic. At a distance of 4 inches above the opossum, the displayed response was strong and continuous.

The experiment demonstrates that it is possible to detect at least one VOC from mammalian body fluids with a portable sensing device. Air currents appear to cause varying concentrations of the VOC and produce fluctuating readings.

In another embodiment, one or more processing steps described herein may be carried out on a handheld electronic device, such as a smartphone, mobile phone, tablet computer, laptop computer, etc. Apparatus 10 may be coupled to the handheld electronic device by wired or wireless technologies (e.g., Universal Serial Bus, Bluetooth short range wireless circuits, Zigbee technology, Wi-Fi technology, etc.). Apparatus 10 may comprise a mount configured to hold the handheld electronic device. An application operating on the handheld electronic device may be configured to control and receive data from apparatus 10. For example, the handheld mobile device may be configured to display the alarms or alerts described herein. The handheld mobile device may be configured to display images or video of the ground taken by a camera disposed as part of sensor 34. Processing of sensor data may take place on handheld mobile device, at circuit 38, or on both. The handheld mobile device may be configured to communicate with a remote server to download updated processing algorithms for improved processing of data from sensors 34 to provide better alerts to the user. Other data relevant to hunting may be displayed on one or more screens of the handheld electronic device, such as time of day, regulated hunting hours, weather radar, other weather-related data, tips for trailing a hunted animal, etc. The function of one or more components described with reference to apparatus 10 may be performed by the handheld mobile device, such as the manually-operable input device which may be replaced by a button on a touch screen of the handheld mobile device. In this manner, the manually-operable input device may be the touch screen or other input device on the handheld mobile device which wirelessly communicates with apparatus 10.

Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

The invention claimed is:

1. A method of trailing a wounded animal, comprising:
providing a sensing device comprising a housing configured to be held in a hand of a person trailing the wounded animal;
swinging the sensing device back and forth over the ground to expose a sensor to airborne compounds from the wounded animal being trailed, wherein the sensing device comprising a control circuit is programmed to discriminate the presence of a chemical component of mammalian blood or other mammalian bodily fluid in the air;
providing an audible and/or visual and/or vibrator indication based on the discrimination of the presence of the chemical component of mammalian blood or other mammalian bodily fluid; and
sweeping the sensing device over the ground to find a next part of a trail left by the wounded animal.

2. The method of claim 1, wherein the sensor is configured to determine the presence of a volatile organic compound.

3. The method of claim 2, further comprising adjusting a sensitivity of the sensor via the control circuit to increase or decrease the sensitivity.

4. The method of claim 1, further comprising comparing a quantity of sensed component to a predetermined threshold via the control circuit and, if the threshold is exceeded, providing the audible and/or visual and/or vibrator indication.

5. The method of claim 4, wherein the predetermined threshold is manually adjustable.

6. The method of claim 1, wherein the sensing device is configured to detect the presence of an aldehyde or a ketone present in mammalian blood.

7. The method of claim 1, further comprising providing a shroud on the housing surrounding an air inlet of the sensing device, wherein the shroud concentrates the ambient air in a headspace above the ground.

8. The method of claim 1, further comprising powering the sensing device by way of a battery coupled to the sensing device and disposed within the housing or apart from the housing and connected by a wire.

9. The method of claim 1, wherein the sensing comprises direct injection mass spectrometry.

10. The method of claim 2, wherein the sensor comprises at least one metal-oxide-semiconductor (MOS) sensor.

11. The method of claim 2, further comprising sensing the chemical component using ion mobility spectrometry.

12. The method of claim 2, wherein the sensor is a discrete, analog aldehyde and ketone alcohol gas sensor component.

13. The method of claim 2, further comprising the sensor using laser light in the detection of the volatile organic compound.

14. The method of claim 1, wherein the sensing device is configured to detect the presence of chemicals in mammalian blood and/or other bodily fluids that have been altered in chemical composition due to exposure to the atmosphere.

15. An apparatus for assisting a person in trailing a wounded animal, comprising:
   an elongated housing at least two feet long comprising a first portion configured to be held in a person's hand and a second portion opposite the first portion having an air inlet;
   a control circuit comprising a sensor, the sensor configured to receive ambient air via the air inlet and to sense a chemical component in the ambient air, wherein the chemical component indicates the presence of mammalian blood or other mammalian bodily fluid in the vicinity of the air inlet, wherein the control circuit is programmed to discriminate from other odors the chemical component indicating the presence of mammalian blood or other mammalian bodily fluid;
   wherein the control circuit is configured to provide an audible and/or visual and/or vibrator indication based on the determination that the mammalian blood or other mammalian bodily fluid is detected; and
   a battery configured to provide power to the control circuit.

16. The apparatus of claim 15, further comprising a manually-operable input device coupled wirelessly or via wire to the control circuit, wherein the control circuit is configured to adjust a sensitivity of the sensing device based on a signal from the manually-operable input device.

17. The apparatus of claim 16, further comprising a memory configured to store a signature representing sensed data for the blood or other bodily fluid to be trailed, wherein the control circuit is configured to receive sensed data, compare the sensed data to the signature, and provide the audible and/or visual and/or vibrator indication based on a result of the comparison.

18. The apparatus of claim 15, wherein the elongated housing weighs less than 10 pounds.

19. A method of trailing a wounded animal, comprising:
   providing a sensing device comprising a housing configured to be held in a hand of a person trailing the wounded animal;
   sweeping the sensing device back and forth over the ground to expose a sensor to airborne compounds from a trail left by the wounded animal, wherein the sensing device is configured to discriminate the presence of a chemical component of mammalian blood or other mammalian bodily fluid in the air, wherein the sensing device provides an audible and/or visual and/or vibrator indication in the presence of the chemical component of mammalian blood or other mammalian bodily fluid; and
   sweeping the sensing device over the ground to find a next part of the trail left by the wounded animal.

20. The method of claim 19, wherein the sensing device is configured to detect the presence of an aldehyde or a ketone present in mammalian blood.

* * * * *